United States Patent
Ahmad (10) Patent No.: US 10,478,094 B1
(45) Date of Patent: Nov. 19, 2019

(54) KETONE MEASUREMENT SYSTEM CAPABLE OF DETERMINING CASUAL COMPONENTS OF A KETONE MEASUREMENT

(71) Applicant: Invoy Holdings, LLC, Aliso Viejo, CA (US)

(72) Inventor: Lubna M. Ahmad, Chandler, AZ (US)

(73) Assignee: Invoy Holdings, LLC, Aliso Viejo, CA (US)

( * ) Notice: Subject to any disclaimer, the term of this patent is extended or adjusted under 35 U.S.C. 154(b) by 0 days.

(21) Appl. No.: 16/361,812

(22) Filed: Mar. 22, 2019

(51) Int. Cl.
| | |
|---|---|
| *A61B 5/083* | (2006.01) |
| *A61B 5/097* | (2006.01) |
| *G01N 33/64* | (2006.01) |
| *A61B 5/00* | (2006.01) |
| *G01N 33/497* | (2006.01) |

(52) U.S. Cl.
CPC .............. *A61B 5/083* (2013.01); *A61B 5/002* (2013.01); *A61B 5/097* (2013.01); *A61B 5/4872* (2013.01); *A61B 5/7275* (2013.01); *G01N 33/497* (2013.01); *G01N 33/64* (2013.01); *G01N 2033/4975* (2013.01)

(58) Field of Classification Search
CPC ....... A61B 5/083; A61B 5/097; A61B 5/4872; G01N 33/64
See application file for complete search history.

(56) References Cited

U.S. PATENT DOCUMENTS

| | | |
|---|---|---|
| 9,341,632 B1 | 5/2016 | Ahmad et al. |
| 9,486,169 B1 | 11/2016 | Ahmad |
| 10,068,494 B2 | 9/2018 | Ahmad et al. |
| 2015/0173648 A1* | 6/2015 | Sano ................ A61B 5/4872 600/532 |
| 2016/0328991 A1* | 11/2016 | Simpson ............ A61B 5/742 |

(Continued)

OTHER PUBLICATIONS

Gajraj, Kim, 'Exogenous ketone supplements: Do they work?', https://www.dietdoctor.com/low-carb/keto/exogenous-ketones, Updated Jan. 1, 2019.

(Continued)

*Primary Examiner* — Herbert K Roberts
(74) *Attorney, Agent, or Firm* — Knobbe, Martens, Olson & Bear, LLP (57) ABSTRACT

A ketone measurement and analysis system provides various features for enabling health program participants to interpret their ketone measurements, such as breath acetone measurements. One such feature breaks down ketone measurements into causal components. For example, the system may generate and display an estimate of how much of a participant's ketone measurement is attributable to stored fat metabolism versus consumption of a "confounding substance" such as dietary fat and/or exogenous ketones. The system may also estimate the contributions of specific confounding substances, and/or the contributions of other factors or events (such as exercise, interrupted sleep, a missed medication, etc.) that affect ketone levels. Another feature involves the generation and display of target ketone levels that are personalized for the participants. The system may generate the measurement breakdowns and target ketone levels by applying data mining algorithms to aggregated data of many program participants.

14 Claims, 5 Drawing Sheets

(56) References Cited

U.S. PATENT DOCUMENTS

2017/0020844 A1* 1/2017 Galinski .............. A61K 31/385
2017/0332951 A1* 11/2017 Ahmad ................. A61B 5/082

OTHER PUBLICATIONS

Kesl, Shannon L., et al., 'Effects of exogenous ketone supplementation on blood ketone, glucose, trigylceride, and lipoprotein levels in Sprague-Dawley rats', Nutrition & Metabolism (2016) 13:9.

* cited by examiner

KETONE MEASUREMENT SYSTEM CAPABLE OF DETERMINING CASUAL COMPONENTS OF A KETONE MEASUREMENT

BACKGROUND

Technical Field

The present invention relates to devices and systems for measuring and analyzing ketone levels in breath, blood, urine, and other bodily fluids.

Description of the Related Art

Fat metabolism is commonly associated with controlled sugar levels (or carbohydrate restriction) and increased energy utilization (e.g., exercise, sexual activity, decreased sleep). Ketone concentrations in bodily fluids such as breath, blood and urine generally increase with increased fat metabolism. As a result, ketone measurements, such as those generated by a breath analysis device that measures levels of acetone (one type of ketone body), can be used to monitor progress on a fat loss program or other health program. Although such ketone measurements are useful, they frequently are not a reliable indicator of fat metabolism.

SUMMARY

Ketone levels in the bodily fluids of a human subject are primarily the result of three factors or processes: (A) metabolism of stored body fat (adipose tissue), (B) ingestion of dietary fat, and (C) ingestion of exogenous ketones by ingestion of ketone supplements such as ketone drinks (e.g., Pruvit® shakes) and ketone bars, which can be of variable chemical composition whether ketone esters, ketone salts or the like. ("Stored body fat" and "dietary fat" are entirely different, even though they both contain the word "fat." "Fat metabolism" refers to the metabolism of stored body fat, and not dietary fat. Exogenous ketone supplements, or simply "ketone supplements," are sometimes used to help the human body remain in, or return to, a state of ketosis in which the body relies on stored body fat as an energy source.) Medium chain triglycerides (e.g., coconut oil and MCT oil) along with a subset of fats generally do not get stored in body fat. Thus, if this subset of fat is consumed, it is generally burned for energy (still resulting in elevated ketone levels). For other fats, once they are digested, they are metabolized in the normal breakdown of fatty acids, which also results in ketone production.

If a human subject consumes approximately the same quantity of dietary fat each day and does not take any ketone supplements, the daily ketone levels of the subject will ordinarily be a much more reliable indicator of fat metabolism. But it is impractical to expect participants in a fat loss program to consume dietary fat at an approximately constant daily rate and to refrain from consuming ketone supplements. To address this issue, one embodiment of the present disclosure provides a ketone measurement system capable of breaking down ketone measurements into causal components. For example, the system may estimate how much of a ketone measurement is attributable to fat metabolism (endogenous ketone generation) versus consumption of a "confounding substance" such as dietary fat and/or exogenous ketones. The system may also be capable of estimating the contributions of specific confounding substances; for example, the system may break down a ketone measurement into a fat metabolism-based component, a dietary fat ingestion-based component, and an exogenous ketone ingestion-based component.

The system may calculate these estimates based on (1) already existing data regarding the typical effects of the confounding substances on ketone levels (e.g., "consumption of Pruvit® shake typically causes breath acetone to increase by 3 to 7 ppm for approximately 24 hours, with a peak occurring after about 60 minute"), and/or (2) data generated by the system by monitoring ketone levels and confounding substance consumption of program participants. The breakdown of the ketone measurement into causal components may be presented to the participant/user via a user interface, and/or may be used by the system to generate more reliable program recommendations (e.g., diet change recommendations) for the user.

The ketone measurement system preferably generates these "attribution estimates" based on information supplied by the user/participant regarding ingestion of one or more of the confounding substances, and based on collected data (user-specific and/or population based) regarding the effects of such confounding substances on ketone levels. For example, in connection with a particular breath ketone test, the user may be prompted, or given the option, to indicate whether, over the last 24 hours (or some other selected time period, such as since their last ketone measurement), they (1) consumed any ketone supplements, and (2) consumed a greater or lesser amount of dietary fat than usual. The user may also be given the option to specify the associated quantities consumed, such as the number of grams consumed of fat and exogenous ketones, respectively.

In some embodiments, the system may also (or alternatively) calculate and display estimates of the contributions of other behaviors or events reported by the user, such as stress, a missed medication, or lack of sleep. The various types of behaviors and events that can affect ketone levels are referred to herein as "ketone factors." Further, in some embodiments the system may generate, and present users with, target ketone levels that are dependent upon the programs of the respective users.

Another problem addressed by the present disclosure involves the management of user expectations regarding ketone levels. The ketone level of a program participant is typically highly dependent upon the particular program, and especially the particular diet, assigned to the participant. For example, those on a low carb diet ordinarily achieve much higher ketone levels than those on a Mediterranean diet. Thus, users on certain programs can become frustrated at their inability to achieve relatively high ketone levels. To address this issue, one aspect of the present disclosure, which may, but need not, be implemented in combination with the features described above, involves generating target or reference ketone levels that take into consideration the health programs assigned to the users. These target or reference levels may be presented, or otherwise used, to assist users in assessing their progress on a particular health program. User expectations can also or alternatively be managed in some embodiments by generating normalized scores that are presented to users in place of their actual ketone levels.

DETAILED DESCRIPTION OF PREFERRED EMBODIMENTS

Figures 1A, 1B:
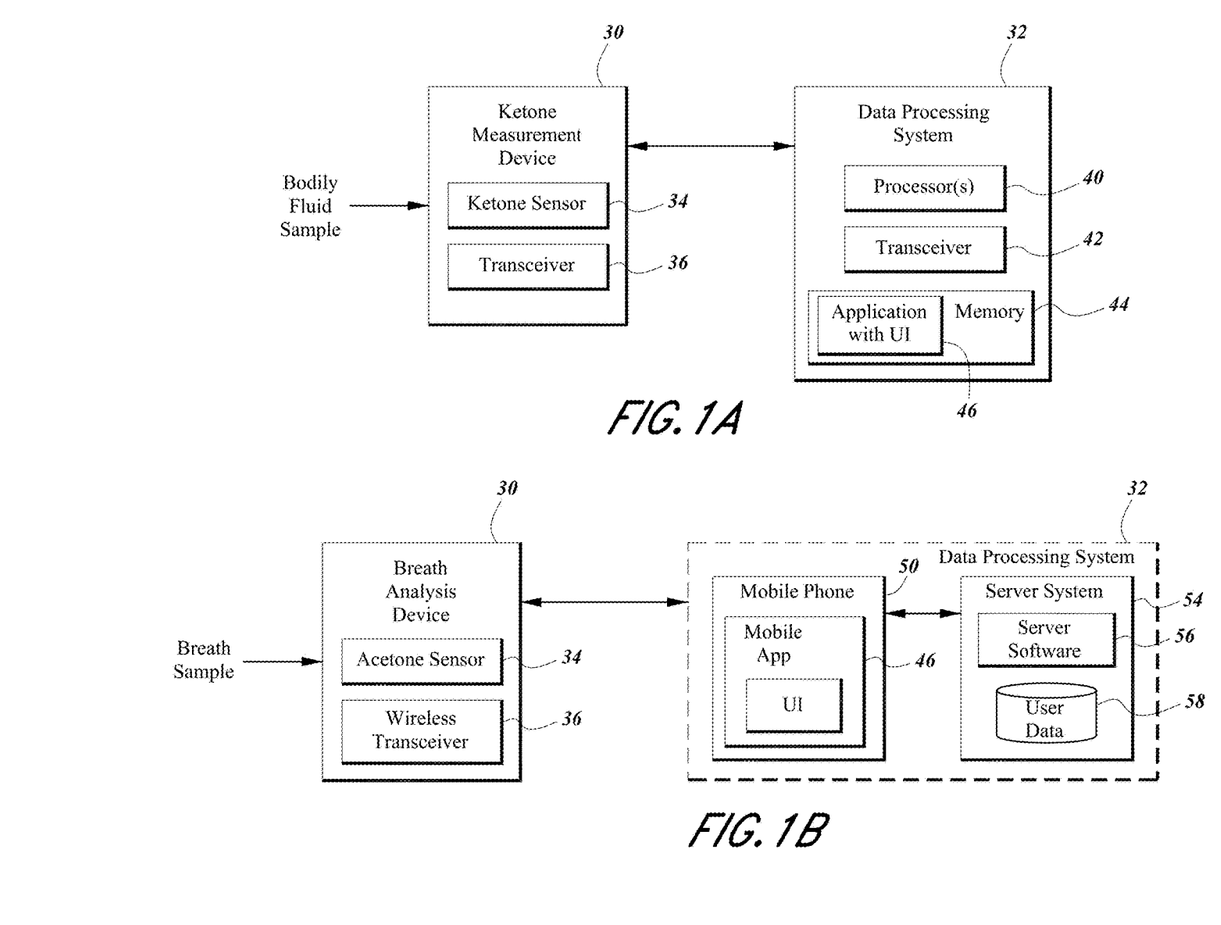
FIG. 1A illustrates a ketone measurement and analysis system according to one embodiment.
FIG. 1B illustrates a more specific embodiment of the system of FIG. 1A.

FIG. 1A illustrates the system according to one embodiment. The system includes a portable (e.g., handheld) ketone measurement device 30 that communicates with a data processing system 32. The ketone measurement device includes a ketone sensor 34, such as a nanoparticle sensor, a colorimetric sensor, an electrochemical sensor, an infrared sensor, or the like that measures a ketone level in a bodily fluid sample (such as a breath, blood, urine, saliva or sweat sample) of a user. The ketone measurement device may vary in configuration depending upon the type of bodily fluid analyzed. For example, ketone measurement devices that analyze blood, urine or saliva samples may be configured to receive and analyze tests strips containing the fluid samples. As another example, the ketone measurement device may be a wearable device that uses an infrared sensor to analyze blood through the skin, or may be a wearable device that measures acetone concentrations in sweat during exercise. The ketone measurement device 30 also includes a transceiver 36, such as a wireless transceiver, for communicating with the data processing system 32. In a typical health program such as a weight loss or fitness program, a ketone measurement device 30 is provided to each program participant and used on a daily basis to monitor progress on the program.

The data processing system 32 can include a single computing device (such as a smartphone, tablet or PC of the user), or can include multiple distinct computing devices that communicate with each other (as shown in FIG. 1B, discussed below). As illustrated, the data processing system 32 includes one or more hardware processors 40, a transceiver 42 that enables it to communicate with the ketone measurement device 30, and a memory (or multiple memories in the case of multiple devices) that stores application software 44 executed by the processor(s) 40. The application software 46 includes a user interface (UI) for enabling the user to interact with the system to, e.g., take and view ketone measurements and monitor progress on a health program. Examples functions and user interface screens that may be implemented in the software application 46 are disclosed in U.S. Pat. No. 9,351,684 and U.S. application Ser. No. 16/232,975, filed Dec. 26, 2018, the disclosures of which are hereby incorporated by reference. As explained below, the user interface may also provide functionality for the user, in connection with specific ketone measurements or measurement cycles, to specify associated ketone factors (including amounts of any confounding substances ingested), and to view information regarding the breakdown of ketone measurements into its causal components. In other embodiments, the ketone measurement device 30 and the data processing system 32 may be combined into a single device.

FIG. 1B illustrates a more specific example of the system of FIG. 1A. In this example, the ketone measurement device 30 is a breath analysis device that analyzes a breath sample of the user, and the ketone sensor is an acetone sensor that measures breath acetone. (Because acetone is volatile, it is released into alveolar air when the blood brings it in contact with the lungs.) Examples of breath analysis devices that may be used are described in U.S. Pat. Nos. 10,226,201 and 9,636,044, U.S. Patent Pub. No. 2016/0331272, and U.S. Provisional Appl. No. 62/773,045, the disclosures of which are hereby incorporated by reference. In some embodiments, the user exhales the breath sample into a breath input port of the breath analysis device; in other embodiments, the user exhales the breath sample into a breath container, such as a breath bag, from which the breath analysis device pumps or otherwise extracts the breath sample for analysis.

In the example system of FIG. 1B, the breath analysis device includes a wireless transceiver, such as a Bluetooth (e.g., Bluetooth Low Energy) or WIFI transceiver, that enables it to communicate with a smartphone 50 or other wireless communication device of the user. The smartphone runs a mobile application 46 that includes a touch-based user interface. In the example of FIG. 1B, the mobile application 46 communicates over a network with a remote server system 54 that runs server software 56. The server system 54 may alternatively be omitted.

The server system 54, where included, may aggregate ketone measurements and other participant data (including demographic data, data reported by the participants regarding ketone factors such as confounding substance consumption, and data indicating the health programs assigned to the users and the time periods of such assignments) in a database 58. The server software 56 may periodically apply a data mining or machine learning algorithm to this aggregated data to generate generalized (population-based) data regarding the impact of specific ketone factors on the ketone levels of users. For instance, the server software may determine from the aggregated data that participants (or those falling within a particular weight range or other class) who consume X grams of excess dietary fat while on a Mediterranean diet experience an average breath ketone level increase of Y parts per million (ppm), and that the increase lasts for roughly one day. The server software 56, and/or the mobile application 46, may also generate similar data that is specific to the particular user/participant. The data processing system 32 may use the population-based and/or user-specific data to break down ketone measurements into causal components.

Figure 2:
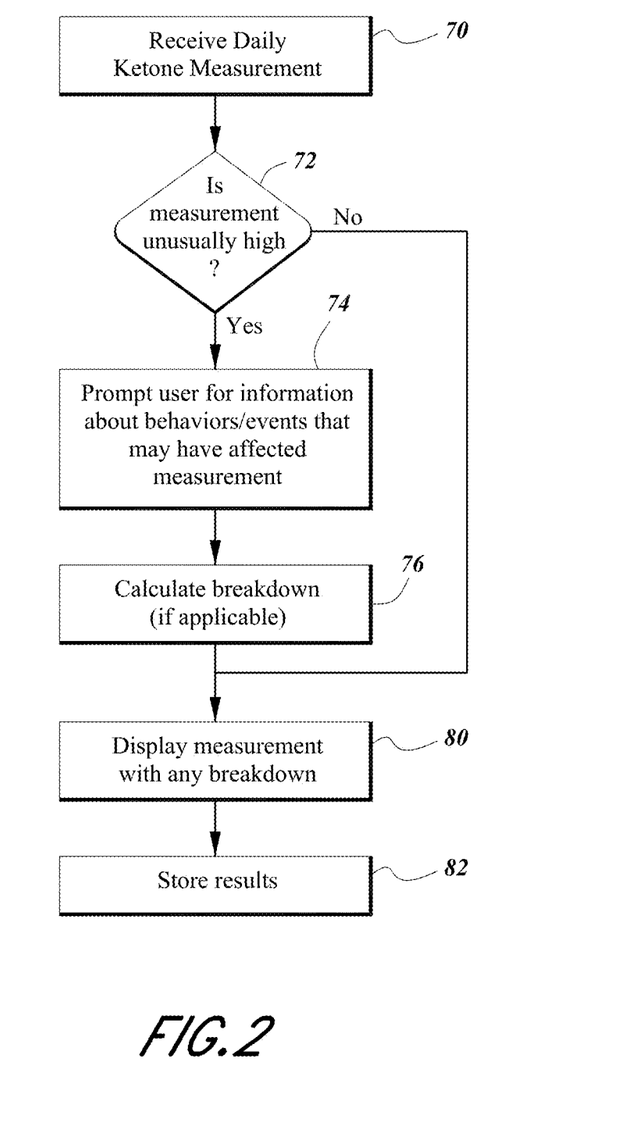
FIG. 2 illustrates a process that may be implemented by the data processing system of FIG. 1A and/or FIG. 1B to process a ketone measurement of a user.

FIG. 2 illustrates one example of a process flow that may be implemented by the data processing system (e.g., by the mobile application 46 of FIG. 1B, or collectively by the mobile application 46 and server software 56) when a user/participant performs a breath test or other ketone test (e.g., a blood-based or urine-based test). In this example, it is assumed that the program participants perform a ketone test once per day, typically at the same time each day (e.g., upon waking up), and that each participant is on a diet that is known to the system. As will be recognized, the process of FIG. 2 can be varied significantly, and is merely one example of how an analysis of confounding substance ingestion may be performed.

Upon receiving the daily ketone measurement (block 70), the process determines whether the measurement is unusually high in comparison to the user's recent measurements (block 72). This may be accomplished by using one or more thresholds. For example, in the case of a breath test, the measurement may be treated as unusual if it is either (1) a change of 3 parts per million from the running average of the past 3 tests, or (2) twice as high as the most recent measurement. Block 72 may alternatively be omitted, in which case the process may proceed to block 74 regardless of whether or how much the user's ketone level increased. In yet another embodiment, the process proceeds to block 74 if the measurement is either unusually high or unusually low.

If the measurement is determined to be unusually high in block 72, the user is prompted to provide information about possible ketone factors (behaviors or events) that may have affected the user's ketone level. This may be accomplished via the mobile application 46 by presenting a user interface that lists possible behaviors/events and prompts the user to select from the list. The list may include some or all of the following, among others: (1) ingestion of a ketone supplement, (2) ingestion of excess dietary fat, (3) missed medication, (4) stressful event, (5) poor sleep, (6) significant exercise beyond daily routine, (7) significant carbohydrate reduction, (8) intermittent fasting, (9) decreased caffeine. If the user indicates that they consumed a ketone supplement and/or excess dietary fat since their last ketone measurement, they may also be prompted to specify the associated amount(s). This list may also be deduced from other information collected by the mobile application such as GPS, heart rate, calendar entries, or step data.

If the user specifies any behaviors or events in block 74, the process in block 76 may calculate a breakdown that attributes one or more portions of the measurement to a particular cause, behavior or event. In some embodiments, block 76 is performed only if the user indicated that they ingested a ketone supplement or excess dietary fat. The breakdown may be calculated based on collected data regarding the effects of confounding substances. The following are examples of such data:

Consumption of an exogenous ketone supplement such as a Pruvit shake typically produces an increase by 3 to 7 ppm in the user's breath acetone level. This increase peaks after about 60 minutes, and lasts for about 24 hours. An increase of 3 to 4 ppm the following morning is typical.

Depending on the type of diet, consumption of excess dietary (or exogenous) fat, for example boluses delivered from MCT oil or "fat bombs," produces an increase by 3 to 7 ppm in the user's breath acetone level. This increase peaks after about 6 hours, and lasts for about 48 hours or longer depending on the amount consumed and regularity of bowel movements.

In block 80, the process displays the measurement to the user together with any breakdown calculated in block 76. Tables 1 through 5 show examples of ketone measurement breakdowns that may be calculated and displayed by the system. A breakdown of the type shown in Table 1 may be presented if, for example, the user reported consumption of a ketone supplement and/or reported excess dietary fat intake, and the amount(s) consumed are attributable to 60% of the measured ketone level.

TABLE 1

Ketone level: 10.8 ppm
Portion attributable to fat loss: 4.3 ppm (40%)

The example of Table 2 is similar, except that the portion attributable to fat loss is further broken down into components based on contributing behaviors reported by the user.

TABLE 2

Ketone level: 10.8 ppm
Portion attributable to fat loss: 4.3 ppm (40%)
20% from decreased carbs
50% from intense workout
30% from active recovery In the example of Table 3, the user has reported consumption of specified quantities of both a ketone supplement and excess dietary fat, and the breakdown shows percentages attributable to each.

TABLE 3

Ketone level: 5.7 ppm
Portion attributable to fat loss: 50%
Portion attributable to ingestion of ketone supplements: 30%
Portion attributable to ingestion of excess dietary fat: 20%

In the example of Table 4, the entire ketone measurement has been determined to be attributable to fat loss. This scenario may arise if, for example, the user did not report consumption of a confounding substance in block 74.

TABLE 4

Ketone level: 7 ppm
Portion attributable to fat loss: 100%

The example of Table 5 is similar to Table 4, but indicates stress as a possible cause for an 40% increase from the user's most recent measurement. This scenario may arise if, for example, the user specifies "stressful event" in block 74 as the only behavior or event that may have affected the measurement.

TABLE 5

Ketone level: 7 ppm
Portion attributable to fat loss: 100%
Possible cause for 40% increase from prior measurement: stress Table 6 illustrates an example in which the user reported a stressful event that was determined to contribute 4 ppm to the user's ketone level.

TABLE 6

Ketone level: 6 ppm
Portion attributable to fat loss: 100%, of which:
3 ppm is attributable to your low-carb diet; and
4 ppm is attributable to your reported stress In block 82, the process stores the measurement results, including the measurement, any associated behaviors or events (ketone factors) reported by the user, and any breakdown of the measurement. The results may be stored both locally on the user's mobile phone 50 and reported to the server system 54, and may be used, in combination with other measurement data of the user, by automated health coaching software to recommend changes to the user's health program. For example, if the ketone measurement is 7 ppm but only 4 ppm is attributable to fat loss, the health coaching software may use the 4 ppm value when evaluating the user's progress on the current program. Examples of software algorithms that may be used by the data processing system 32 to provide automated health coaching (including recommended programs and program changes) are described in U.S. Pat. No. 10,068,494 and U.S. patent application Ser. No. 16/232,975, filed Dec. 26, 2018, the disclosures of which are hereby incorporated by reference.

As mentioned above, the stored measurement data may also be analyzed by the data processing system 32 on a user-specific basis and/or on an aggregated basis to generate user-specific and generalized data, respectively, regarding the effects of the confounding substances (and/or other types of events and behaviors) on ketone levels. This data may, in turn, be used by the system to improve the accuracy of its breakdown calculations.

When analyzing the aggregated or user-specific data to assess the effects of confounding substances on ketone levels, the data processing system 32 may disregard, or give less weight to, events in which the user reported a ketone factor (event or behavior) other than consumption of a confounding substance. For example, if the user reports that they consumed a ketone supplement and also missed a medication, the associated data may be ignored on the basis that the effect of the ketone supplement on the measurement cannot accurately be determined.

Figure 3:
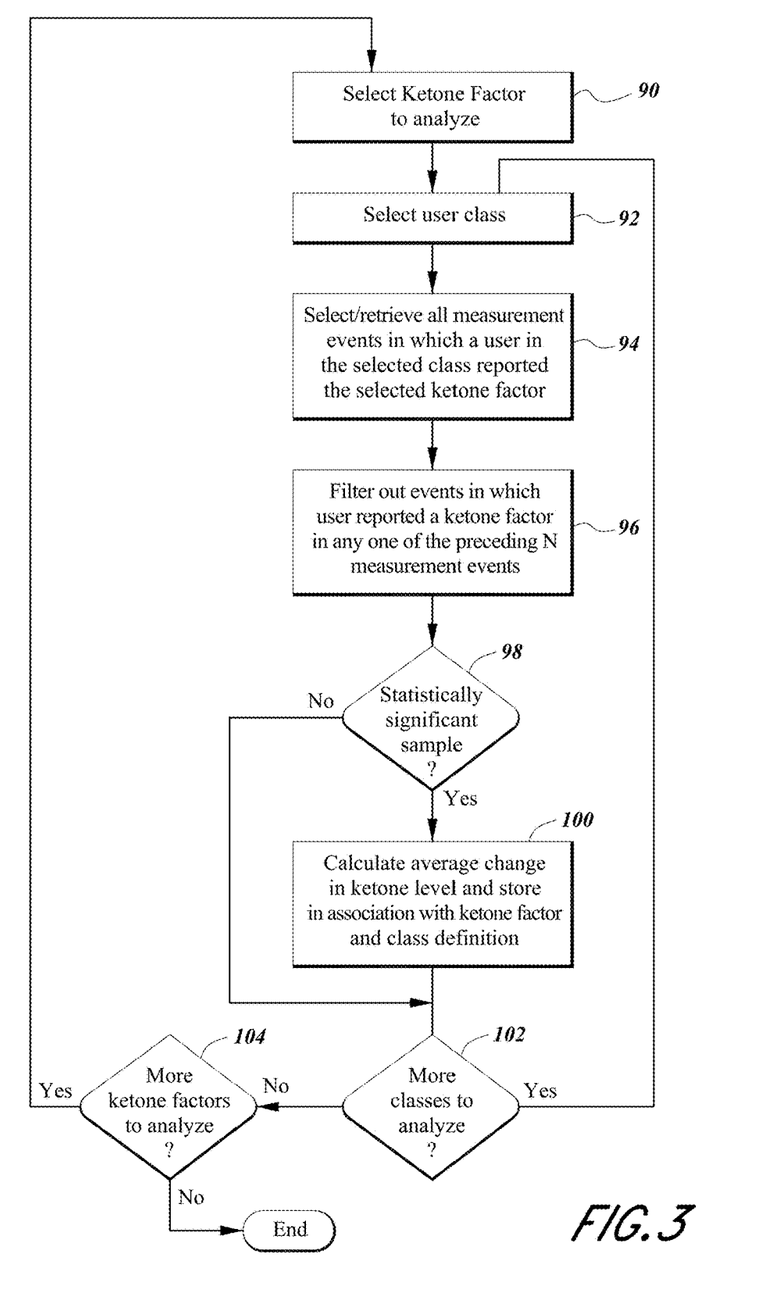
FIG. 3 illustrates a process that may be used by the data processing system of FIG. 1A and/or FIG. 1B to generate data regarding the effects of specific factors on ketone levels of users.

FIG. 3 illustrates a data mining process that can be implemented by the data processing system 32 (e.g., by the server software 56) to generate data regarding the effects of various ketone factors on ketone levels. As explained above, this mined data may be used to generate measurement breakdowns of the type described above. The process of FIG. 3 may be applied to various groups or classes of users to generate generalized data, and may also be applied to the data of a particular user to generate user-specific data for that user.

In block 90, the process selects a ketone factor to analyze. Examples include exogenous ketone consumption (or consumption of a particular amount or type of exogenous ketones), excess dietary fat consumption (generally or of a particular quantity), stress, intense exercise, lack of sleep, and fasting. The ketone factors analyzed preferably match those that are reportable by users via the mobile application's user interface.

In block 92, the process selects a user class to analyze. The following are examples of types of user classes that can be analyzed: all users, all users within a particular weight range, all users on a particular type of diet (e.g., Mediterranean or low-carb), all users on a particular type of health program, users that have been on a health program for at least X weeks, or a particular user. If a particular user is selected, the resulting analysis will be limited to that user's measurement data. A system administrator can define the user classes to be analyzed.

In block 94, the process selects or retrieves from the database 58 (FIG. 1B) all ketone measurement events in which a user falling within the selected class indicated the presence of the selected ketone factor as the only ketone factor. For example, if the selected ketone factor is stress, and the selected user class is all users on a Mediterranean diet, the process would select/retrieve all ketone measurement events in which a user on a Mediterranean diet reported stress in connection with the measurement, but did not report any other ketone factor.

In block 96, the process filters out any events in which the corresponding user reported a ketone factor in connection with one of the N immediately preceding measurements, where N may, e.g., be 1, 2 or 3. For example, if the ketone factor "stress" is being analyzed, N=1, and measurements are taken once per day, the process would filter out all measurements in which the respective user reported a ketone factor (including but not limited to "stress") on the preceding day. This step 96 eliminates from consideration measurement events that are less likely to reveal the effects of the ketone factor of interest on ketone levels.

In block 98, the process determines whether the remaining set of ketone measurement events is sufficiently large to perform a statistically meaningful analysis. For example, a sample size of at least ten (or some other selected number of) measurements may be required. If the sample is of sufficient size, then in block 100 the process calculates the average change in ketone level, and stores this value in association with identifies of the selected ketone level and the selected user class. The average change in block 100 may, for example, be determined relative to immediately preceding ketone measurement of the respective user, or relative to some average, such as a three-day average, of the respective user. For example, the process may determine that the users who reported stress experienced an average breath acetone level increase of 2.7 ppm relative to their immediately preceding measurement.

As represented by blocks 102 and 104 of FIG. 3, the above-described process may be repeated for additional ketone factors and additional user classes.

As mentioned above, the data generated through the process of FIG. 3 may be used to generate measurement breakdowns of the type described above. For example, if a user who performs a breath test reports stress in connection with the measurement cycle, the system may identify a class of which the user is a member and for which data exists on the effects of stress on ketone levels, and may then use this data as the estimated contribution of stress on the user's ketone level. If the user is a member of multiple classes for which such data exists, the process may select the most specific user class, or may take an average (optionally a weighted average) of the data of the multiple classes.

When a user initially starts using the system, the measurement breakdowns presented to the user may be calculated based on generalized (non-user-specific) data regarding the effects of ketone factors. Over time, the system may learn, based on the user's ketone measurements and reported behaviors/events, how particular ketone factors affect the user's ketone levels, and may use this data to provide more accurate breakdowns of the user's measurements. Table 7 below illustrates one example of a "phase-in" schedule that the system may use to transition from population-based to user-specific data in generating measurement breakdowns for a user.

TABLE 7

Reliance on population-based versus user-specific data to calculate breakdowns

| Week | Population-based data | User-specific data |
|---|---|---|
| 1 | 100% | 0% |
| 2 | 90% | 10% |
| 3 | 80% | 20% |
| 4 | 70% | 30% |
| 5 | 60% | 40% |
| 6 | 50% | 50% |
| 7 and after | 40% | 60% |

Types of Exogenous Ketones

Multiple types of exogenous ketones exist, including ketone salts and various ketone esters. In some embodiments, different exogenous ketone types may be treated as different ketone factors. For example, users may be given the option to specify the type of exogenous ketone ingested in block 74 of FIG. 2, either directly or by specifying the product name or trade name of the supplement consumed.

Adjusting Ketone Measurements to Compensate for Certain Ketone Factors

In some embodiments, the system may adjust ketone measurements to compensate for ketone factors reported by the user. For example, the process of FIG. 2 may be varied as follows. Upon receiving the ketone measurement in block 70, the data processing system 32 (e.g., mobile application 46) may prompt the user to indicate whether they experienced any ketone factors other than exogenous ketone ingestion or excess dietary fat ingestion. For example, the user may be prompted to indicate whether they missed a medication, experienced unusually high stress, or experienced interrupted sleep. If the user indicates that one or more of these events occurred, the system may adjust the measurement to compensate for the event, as described in U.S. Pat. No. 9,486,169, the disclosure of which is incorporated by reference. The data processing system may then determine whether the measurement, as adjusted, is unusually high (block 74), and if it is, prompt the user in block 76 to indicate whether they ingested a ketone supplement or excess dietary fat. The remainder of the process of FIG. 2 may remain the same.

Reference Ketone Levels

The ketone level of a program participant is typically highly dependent upon the particular program, and especially the particular diet, assigned to the participant. For example, a typical breath acetone level for an individual on a low carb diet is 7 ppm, while the typical breath acetone level for an individual on a Mediterranean diet is 1.5 ppm. The typical ketone levels are also highly dependent upon any accelerants included in the program. Examples of accelerants include exercise, intermittent fasting, planned cheat meals, decreased alcohol consumption, decreased stimulants (e.g., coffee/caffeine), and consumption of supplements (e.g., BCAs, magnesium, etc.). Accelerants are not substitutes or replacements for food plans, but rather help boost the impact of the overall program so that users can achieve their goals faster. Additional information regarding accelerants can be found in U.S. patent application Ser. No. 16/232,975, filed Dec. 26, 2018, the disclosure of which is hereby incorporated by reference.

Because ketone levels are highly program-dependent, and because participants are sometimes switched from one program to another (e.g., when the participant reaches a plateau), it is desirable to manage user expectations regarding their ketone levels. In some embodiments, the system manages user expectations by generating, and communicating to each user via the mobile application 46, a reference ketone level, such as a target ketone level, that is dependent upon the particular program assigned to the user. For example, if a user switches from a low carb diet to a Mediterranean diet, the user's reference ketone level will ordinarily be decreased by an amount that depends on typical ketone levels of participants on low carb versus Mediterranean diets. By informing the user of their new reference ketone level, the system reduces the likelihood that the user will become frustrated when ketone levels decline under the new program. In some embodiments, the each ketone measurement may be displayed to the user together with, or relative to, the user's reference ketone level. Preferably, but not necessarily, the reference ketone levels are based on the average ketone measurements of similarly situated participants, as described below. The reference ketone levels preferably serve as targets for the participants, and are therefore referred to herein as "target ketone levels."

The data processing system 32 may generate the target ketone levels or scores using the aggregated user data 58 it collects. For example, to generate the target ketone level for a user on a program that includes a particular diet and a particular set of one or more accelerants, the system 32 may analyze (e.g., take the average of) the reported ketone levels of some or all participants that are (or were) on this diet and set of accelerants. The system 32 may also optionally take into consideration the profile (e.g., weight, age, gender, ketone level history, goals, metabolic classification, etc.) of the particular user, so that the target level is personalized for the user.

For instance, suppose a user is on a program that includes (1) a low carb diet and (2) a specified amount of weight training exercise as an accelerant. Based on the ketone measurements of other users who have been on the same or a similar program (and ideally those with profiles similar to that of this user), the system 32 may generate a reference or "target" breath acetone level of 8 ppm, and communicate this value to the user via the application 46. The user's breath acetone level may thereafter be measured as 5 ppm, possibly because the user has not been fully engaged in the weight training component during the last few days. In addition to informing the user of the actual ketone level and target level, the system may generate a breakdown, as described above, of the 5 ppm measurement. If sufficient data has been collected from the user regarding the user's recent behaviors, the breakdown may indicate to the user that the 3 ppm deficiency relative to the target is likely attributable to insufficient weight training.

Figure 4:
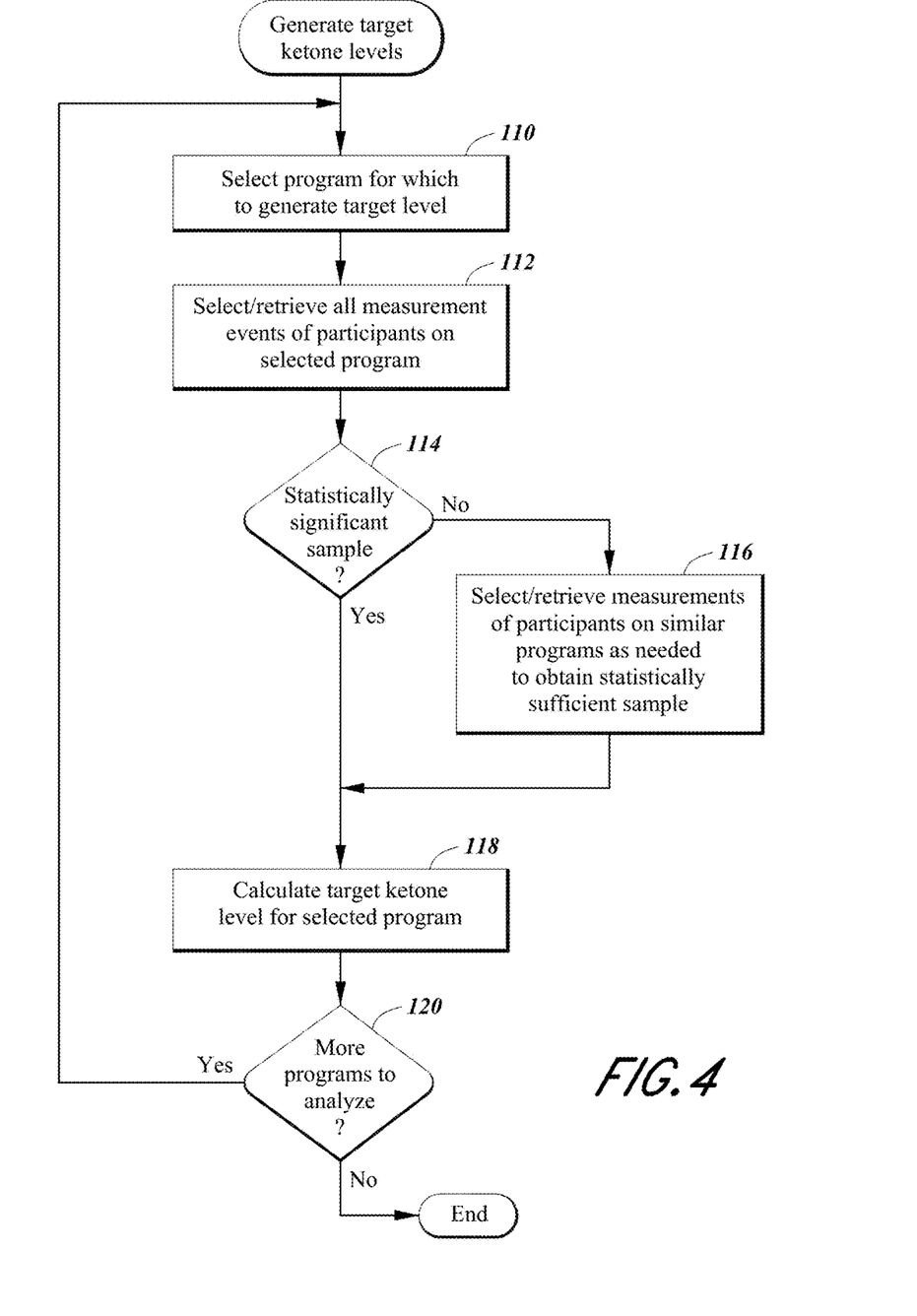
FIG. 4 illustrates a process that may be used by the data processing system of FIG. 1A and/or FIG. 1B to generate reference (e.g., target) ketone levels for particular programs and participants.

FIG. 4 further illustrates a process that may be implemented by the data processing system 32 to generate reference ketone levels, such as target ketone levels, for various health programs. This process may be embodied in the server software 56 (FIG. 1B) executed by the server system 54. In block 110, the process selects a program to analyze, and in block 112, the process retrieves the measurement event data collected for participants on the selected program. As mentioned above, a health program may include a diet/food plan and one or more accelerants, although this is not intended to be limiting. In some cases, many dozens to hundreds of health programs may be defined within the system, and each may be separately analyzed to generate one or more corresponding reference ketone levels.

In block 114 of FIG. 4, the process determines whether the quantity of measurement event data is sufficient to generate a statistically significant result. One or more pre-programmed thresholds may be used for this purpose; for example, the process may require at least one hundred ketone measurements of at least ten distinct program participants. If the sample size is too small, the process may supplement the sample (block 116) with measurement event data of participants on similar programs. Two programs may be treated as similar if, for example, they share a common food plan and differ by no more than one accelerant.

In block 118, the system uses the retrieved measurement event data to generate a target ketone level for the selected program. The reference or target level may, for example, be generated by taking the average or mean of (1) all measurements retrieved in blocks 112 and 116, or (2) only the retrieved measurements of those who, at the time of the measurement, reported or achieved satisfactory results (e.g., weight loss, subjective program satisfaction, etc.). In embodiments in which the reference ketone level is presented to users as a target, this value may optionally be increased by a selected amount, such as 5% or 10% (or by an amount that depends upon goals specified by the user), so the target exceeds the average or mean. One variation in block 118 is to give more weight to some measurements than to others; for example, more weight can be given to the ketone measurements of participants on the selected program than to measurements of participants on similar programs. As represented by block 120, the process may be repeated for each program defined within the system. The results (target ketone levels for particular health programs) may be stored for subsequent lookup.

One variation of the FIG. 4 process is to generate reference ketone levels for particular user classes, such as those within a particular weight range or those having a particular metabolic profile. For example, once a program is selected in block 110, the process may select a particular user class to analyze, and may determine whether sufficient measurement data exists for members of the class who participated on the selected program. Thus, multiple, user-class-specific reference (e.g., target) ketone levels may be generated for a given health program.

Another variation to the FIG. 4 process is to additionally generate average weight loss data for particular programs (and optionally for multiple user classes within each program). For example, assuming the data processing system 32 records weight levels of the program participants (as reported by the participants or collected from wireless scales, for example), the process may use the measurement event data retrieved in blocks 112 and 116 to calculate the average weight loss over selected period(s) of time, such as two weeks, one month, two months, etc. For example, the process may determine that participants (or those in a particular user class) on a program that includes a low carb diet and a particular accelerant achieve an average weight loss of 11.8 pounds during the first month of the program. This average weight loss data may be presented to the program participants to assist them in evaluating their own progress. In addition, the mobile application may present users with an interactive user interface through which a user can, at the time of choosing between multiple program options, view the average weight loss data associated with each such option.

Figure 5:
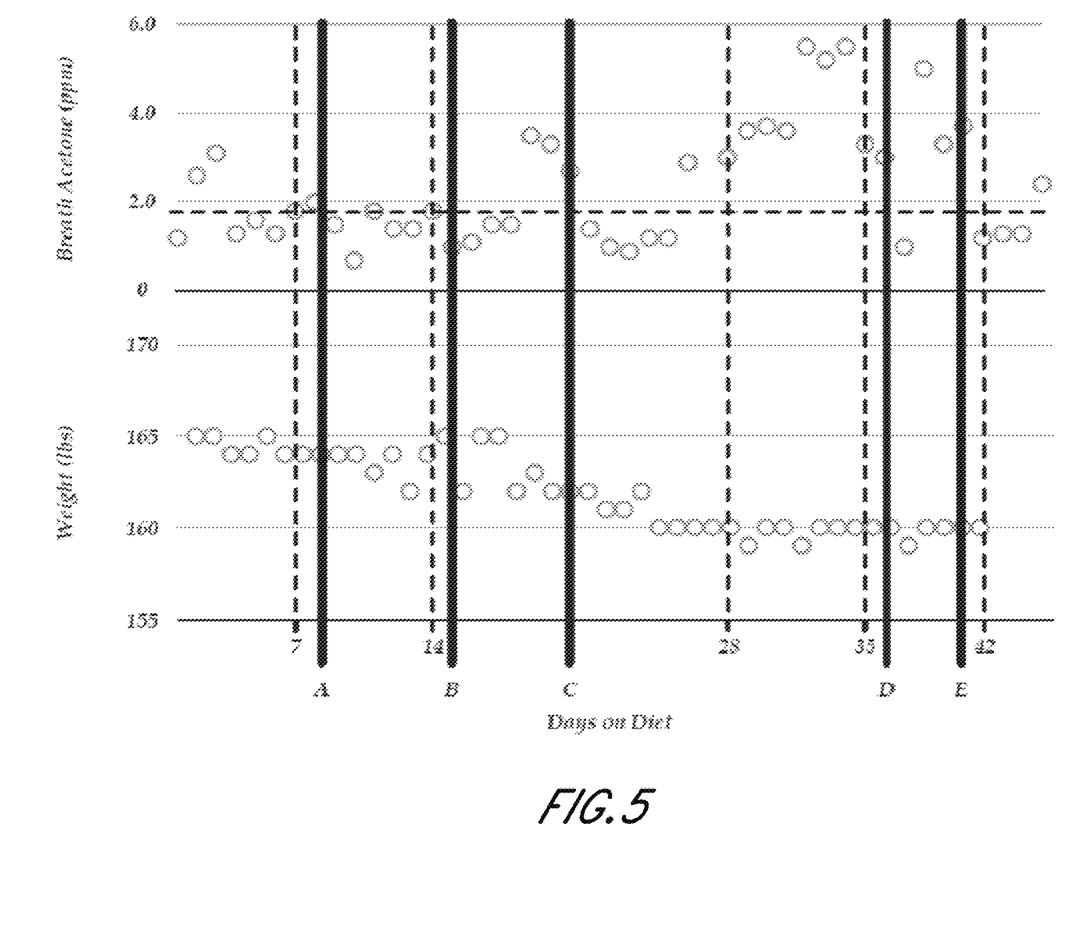
FIG. 5 illustrates one example of a user interface that may be generated by the data processing system of FIGS. 1A and/or 1B to enable users to view their ketone measurements relative to a reference ketone level.

FIG. 5 shows one example of a user interface that displays ketone (breath acetone) measurements of a program participant relative to a reference (e.g., target) ketone level, which is represented by the horizontal dashed line. The data processing system 32 may present this type of user interface to the program participant, and/or to a health coach of the participant, via the mobile application 46 or a web-based interface. The horizontal or x-axis represents time, and more specifically the number of days the user has been on a particular program. The upper portion of the vertical or y-axis represents the user's breath acetone concentration (in ppm) as measured using a breath analysis device 30 on the day corresponding to the associated position on the x-axis. The lower portion of the vertical or y-axis represents the user's body weight (in pounds or "lbs.") measured at the time of acetone measurement (e.g., using a standard weight scale). The weight measurements may alternatively be omitted from the display. The breath acetone measurements are taken each morning, so each data point in the upper portion of the plot represents a one-day measurement. The vertical bars labeled A, B, C and D represent program non-compliance events reported by the user, and are helpful for interpreting the data. This user interface enables the user to easily compare the breath acetone measurements to the target breath acetone measurement generated by the system, and thus enables the user to more effectively assess his or her progress on the program. The target level in this example may be generated by the process of FIG. 4, and may correspond to the particular health program assigned to the user. The target level may, in some embodiments, be personalized for the user; for example, if the user has selected a goal of "aggressive weight loss," the system may display a target level that is higher (e.g., by 10%) than the level calculated in FIG. 4 for the user's program.

As described in the following section, the reference/target ketone levels need not be displayed to user, but may alternatively be used to generate normalized scores that are conveyed to users.

Normalized Ketone Scores and Status Indicators

In some embodiments, the system 32 may additionally or alternatively manage user expectations by generating a normalized score that is presented to the user (e.g., via the mobile application 46) in place of the actual ketone level. The normalized scores are preferably generated so as to mask or conceal from the user the effects of the assigned health program on the user's ketone scores. As one example, the normalized score (which may be referred to as a "target fat burn" number or "target score") can be generated by taking the ratio of the actual ketone level to the target ketone level, where the target ketone level may be generated as described above. With this approach, a normalized score of 1 or above indicates that the user's ketone level is at or above the target, and a normalized score below 1 indicates that the ketone level is below the target.

For instance, if the system determines a target ketone level of 8 ppm for a user on a low carb diet, and the user's actual ketone level is 6 ppm, the system may generate and display a normalized score of 6/8=0.75 (which may be presented as "75" or "75% of target"). If the user is switched to a Mediterranean diet, the system may adjust the target ketone level to a lower value such as 2 ppm; if the user's ketone level is then measured at 1.7 ppm, the system may calculate and display a normalized score of 1.7/2=0.85 (which may be displayed as "85" or "85% of target"). Note that the actual ketone levels in these examples preferably are not presented to the user.

In yet other embodiments, the system 32 may, instead of presenting users with ketone levels or normalized scores, present the user with non-numeric progress indicators. For example, the system may use a "traffic light" style display in which green represents good performance, yellow represents an intermediate level of performance, and red represents poor performance. Each such color may correspond to a particular range of normalized scores; for example, if the normalized scores are calculated as described above, a normalized score of 1 or above may be represented as green, a score of 0.6 to 0.99 may be represented as yellow, and a normalized score of less than 0.6 may be represented as red.

CONCLUSION

All of the actions described herein as being performed by "the system" or "data processing system" may be performed under the control of program instructions executed by, e.g., (1) a server machine or group of machines, (2) a mobile device 50 of a user under control of the mobile application 46, or (3) a combination of (1) and (2). Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the system. Where the computer system includes multiple computing devices, these devices may, but need not, be co-located. The results of the disclosed methods and tasks may be persistently stored by transforming physical storage devices, such as solid state memory chips and/or magnetic disks, into a different state. In some embodiments, the computer system may be a cloud-based computing system.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A system, comprising:
    a breath analysis device, the breath analysis device comprising a breath input port that receives a breath sample of a user and a ketone sensor that generates a breath ketone measurement representing a ketone level in the breath sample, the breath analysis device further comprising a wireless transceiver;
    a data processing system comprising one or more processors and a wireless transceiver, the data processing system configured to communicate wirelessly with the breath analysis device and to receive from the breath analysis device a data value representing the breath ketone measurement, the data processing system comprising a user interface that prompts the user to supply, in association with breath sample, data regarding ingestion by the user of a confounding substance, including data regarding ingestion by the user of excess dietary fat;
    wherein the data processing system is configured to generate, based on the data regarding ingestion by the user of a confounding substance, an estimate of a portion of the breath ketone measurement that is attributable to metabolism of stored fat, and is programmed to generate, and display in the user interface, a breakdown of the breath ketone measurement into at least a portion caused by metabolism of stored fat and a portion not caused by metabolism of stored fat, wherein the breakdown further indicates, for the portion not caused by metabolism of stored fat, how much is attributable to consumption of excess dietary fat.

2. The system of claim 1, wherein the data regarding ingestion of a confounding substance comprises an indication of whether the user consumed a ketone supplement.

3. The system of claim 1, wherein the data processing system is programmed to generate the estimate based at least partly on user-specific data reflective of how much the ketone level of the user has previously increased in response to ingestion by the user of the confounding substance.

4. The system of claim 1, wherein the breakdown further indicates, for the portion not caused by fat metabolism of stored fat, how much is attributable to consumption of a ketone supplement.

5. The system of claim 1, wherein the breakdown further indicates how much of the portion caused by metabolism of stored fat is attributable to a particular factor.

6. The system of claim 5, wherein the particular factor is one of the following: stress, a missed medication, exercise, irregular sleep, a diet change.

7. The system of claim 1, wherein the data processing system is programmed to analyze aggregated measurement data of users, including ketone measurements of the users and confounding substance consumption events reported by the users, to generate data regarding effects of particular confounding substances on ketone levels of users.

8. A system, comprising:
    a ketone measurement device configured to receive a bodily fluid sample of a user, the ketone measurement device comprising a ketone sensor that generates a ketone measurement representing a ketone level in the bodily fluid sample, the ketone measurement device further comprising a transceiver;
    a data processing system comprising one or more processors and a transceiver, the data processing system configured to communicate with the ketone measurement device and to receive from the ketone measurement device a data value representing the ketone measurement, the data processing system comprising a user interface that prompts the user to supply, in association with the bodily fluid sample, data regarding one or more ketone factors that may have affected the measurement, wherein the data regarding one or more ketone factors comprises data regarding ingestion by the user of excess dietary fat, and the data processing system is configured to generate an estimate of how much of the ketone measurement is attributable to ingestion of excess dietary fat;
    wherein the data processing system is configured to generate, based on the data regarding the one or more ketone factors, an estimate of a portion of the ketone measurement that is attributable to the ingestion of excess dietary fat, and is configured to generate, and display in the user interface, a breakdown of the measurement into multiple portions, including said portion attributable to the ingestion of excess dietary fat and a portion attributable to metabolism of stored body fat.

9. The system of claim 8, wherein the data regarding one or more ketone factors comprises data regarding ingestion by the user of a ketone supplement, and the data processing system is configured to generate an estimate of how much of the ketone measurement is attributable to ingestion of the ketone supplement.

10. The system of claim 8, wherein the data regarding one or more ketone factors comprises data regarding a plurality of ketone factors, and the data processing system is configured to generate an estimate of how much each of the plurality of ketone factors contributed to the ketone measurement.

11. The system of claim 8, wherein the data processing system is additionally configured to generate, and communicate to the user, a target ketone level for the user, said target based at least partly on a program currently assigned to the user, and ketone measurements of other users on the program.

12. A method, comprising:
   generating, with a breath analysis device, a ketone measurement representing a ketone level in a breath sample of a user;
   receiving, in association with the breath sample, data regarding ingestion by the user of a confounding substance, wherein the data regarding ingestion by the user of a confounding substance comprises an indication supplied by the user of excess fat consumption by the user;
   generating, by execution of program code by a data processing system, based on said data, at least (1) an estimate of a portion of the ketone measurement that is attributable to metabolism of stored fat, and (2) an estimate of a portion of the ketone measurement that is attributable to excess dietary fat consumption; and
   generating, and outputting via a user interface, a measurement breakdown indicating at least the estimate of the portion attributable to the metabolism of stored fat and the estimate of the portion attributable to excess dietary fat consumption.

13. The method of claim 12, wherein the data regarding ingestion of a confounding substance additionally comprises data regarding ketone supplement ingestion by the user.

14. A method, comprising:
   generating, with a breath analysis device, a breath ketone measurement representing a ketone level in a breath sample of a user;
   determining, by execution of program code by a processor, that the breath ketone measurement has increased by at least a threshold amount relative to one or more prior breath ketone measurements of the user;
   in response to determining that the breath ketone measurement has increased by at least the threshold amount, generating a user interface that prompts the user to indicate, at least, an amount of excess dietary fat consumed by the user within a specified time period;
   receiving, via the user interface, user input indicating said amount of excess dietary fat consumed; and
   generating, and outputting for display, a measurement breakdown indicating, at least, an amount of the breath ketone measurement that is attributable to excess dietary fat consumption and an amount of the breath ketone measurement that is attributable to metabolism of stored fat.

* * * * *